US012332157B2

(12) United States Patent
Camargo et al.

(10) Patent No.: US 12,332,157 B2
(45) Date of Patent: Jun. 17, 2025

(54) METHODS AND SYSTEMS FOR DETERMINING RESERVOIR AND FRACTURE PROPERTIES

(71) Applicant: Saudi Arabian Oil Company, Dhahran (SA)

(72) Inventors: Otto Meza Camargo, Dhahran (SA); Tariq Mahmood, Dhahran (SA); Khalid Hawas, Dhahran (SA); Antonio Santagati, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 810 days.

(21) Appl. No.: 17/237,284

(22) Filed: Apr. 22, 2021

(65) Prior Publication Data

US 2022/0341835 A1 Oct. 27, 2022

(51) Int. Cl.
*G01N 15/08* (2006.01)
*E21B 47/002* (2012.01)
(Continued)

(52) U.S. Cl.
CPC .......... *G01N 15/088* (2013.01); *E21B 49/02* (2013.01); *G01N 33/241* (2013.01); *G01V 20/00* (2024.01);
(Continued)

(58) Field of Classification Search
CPC .... E21B 2200/20; E21B 43/26; E21B 47/002; E21B 49/02; G01N 15/088; G01N 33/241; G01V 99/005
See application file for complete search history.

(56) References Cited

U.S. PATENT DOCUMENTS

| 4,911,002 A * | 3/1990 | Enderlin .................. G01N 3/40 318/490 |
| 5,430,291 A * | 7/1995 | Pepin .................. G01N 23/046 378/4 |

(Continued)

FOREIGN PATENT DOCUMENTS

| CN | 103198363 A | 7/2013 |
| CN | 106096249 A | 11/2016 |

(Continued)

OTHER PUBLICATIONS

Zhu, CN 104359817, English Translation (Year: 2014).*
(Continued)

*Primary Examiner* — Michael J Dalbo
(74) *Attorney, Agent, or Firm* — Bracewell LLP; Constance G. Rhebergen; Keith R. Derrington

(57) ABSTRACT

Methods and systems for determining pore-volume of a fracture in a core plug. The method includes developing a grid block model constrained by fracture porosity estimated from a mechanical laboratory test, aperture calculation, and discrete fracture model validation. The method further includes determining the natural fracture porosity and pore volume from the equivalent medium for natural fractures, determining oil or gas reserves by calculating the fracture pore volume, and determining fracture porosity measurement from a test to calibrate 3D fracture models. The method also includes determining fracture porosity from a mechanical test, analyzing borehole image logs, developing a geomechanical model and fracture drivers, performing fracture model predictions, validating and calibrating the model, and determining fracture pore-volume of the core plug.

12 Claims, 15 Drawing Sheets

(51) Int. Cl.
  *E21B 49/02* (2006.01)
  *G01N 33/24* (2006.01)
  *G01V 20/00* (2024.01)
(52) U.S. Cl.
  CPC ......... *E21B 47/002* (2020.05); *E21B 2200/20* (2020.05)

(56) References Cited

U.S. PATENT DOCUMENTS

| | | | |
|---|---|---|---|
| 8,805,661 B2 | 8/2014 | Li et al. | |
| 2009/0248309 A1* | 10/2009 | Neville | G01V 5/107 250/269.4 |
| 2013/0096889 A1* | 4/2013 | Khvoenkova | G01V 20/00 703/2 |
| 2014/0136172 A1* | 5/2014 | Gorell | G01V 9/00 703/10 |
| 2016/0123119 A1* | 5/2016 | Tueckmantel | E21B 43/26 703/10 |
| 2016/0355727 A1* | 12/2016 | Barati Ghahfarokhi | C09K 8/80 |
| 2017/0052272 A1* | 2/2017 | Maeso | G01V 3/20 |
| 2017/0275970 A1* | 9/2017 | Crawford | G01V 20/00 |
| 2019/0080122 A1* | 3/2019 | Camargo | G06F 30/20 |
| 2020/0095858 A1* | 3/2020 | Bouaouaja | G01V 1/46 |
| 2022/0291418 A1* | 9/2022 | Noufal | G01V 1/306 |
| 2023/0296580 A1* | 9/2023 | Akbarabadi | C09K 8/58 507/202 |

FOREIGN PATENT DOCUMENTS

| | | |
|---|---|---|
| CN | 107449707 A | 12/2017 |
| CN | 108590642 A | 9/2018 |
| CN | 109490165 A | 3/2019 |
| CN | 109887083 A | 6/2019 |
| CN | 110244023 A | 9/2019 |
| CN | 110472276 A | 11/2019 |
| CN | 110568160 A | 12/2019 |
| CN | 110704888 A | 1/2020 |

OTHER PUBLICATIONS

Torres WO-2016051345, English Translation (Year: 2016).*
Hou, CN 103616731, English translation (Year: 2014).*
ASTM International; "Standard Practices for Preparing Rock Core as Cylindrical Test Speciments and Verifying Conformance to Dimensional and Shape Tolerances" Designation: D4543-08, Feb. 2008; pp. 1-9.
ASTM International; "Standard Test Methods for Compressive Strength and Elastic Moduli of Intact Rock Core Speciments under Varying States of Stress and Temperatures" Designation: D7012-14, Jun. 2014; pp. 1-9.
Barton, Colleen A. et al.; "Fluid flow along potentially active faults in crystalline rock" Geology; Aug. 1995; v. 23; No. 8; pp. 683-686.
Herwanger, J. et al.; "Seismic Geomechanics: How to Build and Calibrate Geomechanical Models using 3D and 4D Seismic Data" European Association of Geoscientists & Engineers (EAGE) 2011; pp. 1-174.
Lei, Qinghua et al.; "The use of discrete fracture networks for modelling coupled geomechanical and hydrological behaviour of fractured rocks" Computers and Geotechnics 85 (2017); pp. 151-176.
Maerten, F.; "Adaptive cross-approximation applied to the solution of system of equations and post-processing for 3D elastostatic problems using the boundary element method" Engineering Analysis with Boundary Elements 34 (2010); pp. 483-491.
Min, Ki-Bok et al.; "Stress-Dependent Permeability of Fractured Rock Masses: A Numerical Study" International Journal of Rock Mechanics & Mining Sciences, vol. 41, Issue 7, Apr. 30, 2004; pp. 1-58.
Zimmerman, R.W.; "compressibility of sandstones" Developments in Petroleim Science 29, Elsevier 1991; pp. 1-183.
Zoback, Mark D.; "Chapter 11: Critically stressed faults and fluid flow" Reservoir Geomechanics, Cambridge University Press, 2007; pp. 1-21.
Marko Maucec et al., "New Approach to History Matching of Simulation Models with Discrete Fracture Networks", International Petroleum Technology Conference, Jan. 13, 2020, XP055703162.
International Search Report and Written Opinion for PCT Application No. PCT/US2022/025984 dated Jul. 7, 2022.
Saudi Arabian 1st Examination Report, Application No. 523451218, dated Aug. 29, 2024.

* cited by examiner

METHODS AND SYSTEMS FOR DETERMINING RESERVOIR AND FRACTURE PROPERTIES

TECHNICAL FIELD

Embodiments generally relate to methods for determining formation properties, and more specifically relate to methods and systems for determining reservoir and fracture properties.

BACKGROUND

Determination of flow properties of extremely low permeability source rocks or tight reservoirs is critical for optimum field development planning. Conventional well testing or rate transient analysis methods applied to hydraulically fractured horizontal wells in such reservoirs are impractical due to the very long testing periods needed to obtain reservoir properties and fracture surface areas along the well trajectory, which prevents evaluation of production performance of individual fractures. In addition, conventional well tests disturb initial reservoir conditions with continuous injection/production rates.

In general, the rock pore-volume can be estimated using rock bulk volume and matrix porosity, assuming that matrix contains total pore-volume and total oil and gas reserves. However, conventional wireline logs such as neutron density, bulk density, and acoustic sonic logs are not able to capture or detect the natural fracture presence or quantify direct or indirectly the fracture porosity for naturally fractures reservoir environments. This assumption probably neglects the fractures storage capacity that could be properly reflected through a dual porosity and dual permeability system.

Natural fractures can significantly improve reservoir connectivity, enhancing the total permeability for the earth geological model, but also serving as "fluid storage" in highly fractured environments such as carbonates reservoirs.

SUMMARY

The quantification of fracture porosity from a natural fracture network depends of several components that should be characterized in order to capture the fracture features observed from core and log analysis into the model. Those components include the fracture position, fracture intensity, fracture geometry, and fracture aperture.

Therefore there is a need for improved methods and systems for more accurately determining reservoir and fracture properties by taking into consideration several components in order to capture the fracture features observed from core and log analysis into the model. The natural fracture pore-volume quantification corresponding to naturally fractures reservoir can be estimated when a reliable and predictive three-dimensional (3D) natural fracture network is constructed, following the natural fracture prediction workflows.

Accordingly, one embodiment is a method for fracture pore-volume quantification for a grid block model, constrained by fracture porosity estimated from mechanical laboratory test, aperture calculation, and discrete fracture model validation. The method includes obtaining the natural fracture porosity and pore volume from the equivalent medium for natural fractures, obtaining oil/gas reserves by calculating the fracture pore volume, and obtaining fracture porosity measurement from tests to calibrate 3D fracture models. Natural fractures can significantly improve reservoir connectivity, enhancing the total permeability for the earth geological model, but also serving as "fluid storage" in highly fractured environments such as carbonates reservoirs. The quantification of fracture porosity from a natural fracture network depends on fracture position, fracture intensity, fracture geometry and fracture aperture.

One example embodiment is a method for determining pore-volume of a fracture in a core plug. The method includes developing a grid block model constrained by fracture porosity estimated from a mechanical laboratory test, aperture calculation, and discrete fracture model validation. The method further includes determining the natural fracture porosity and pore volume from the equivalent medium for natural fractures, determining oil or gas reserves by calculating the fracture pore volume, and determining fracture porosity measurement from a test to calibrate 3D fracture models. The method also includes determining fracture porosity from a mechanical test, analyzing borehole image logs, developing a geomechanical model and fracture drivers, performing fracture model predictions, validating and calibrating the model, and determining fracture pore-volume of the core plug.

The step of determining fracture porosity from a mechanical test further includes selecting an intact core plug, performing a conventional core analysis for porosity and permeability of the core plug; and determining stress dependency of the porosity and permeability of the intact core plug. The step of determining fracture porosity from a mechanical test further includes selecting a fractured core plug, determining fracture porosity and permeability of the fractured core plug, and determining stress dependency of the porosity and permeability of the fractured core plug. The step of analyzing borehole image logs further includes calibration of core image logs, performing aperture calculations, and determining fracture intensity based on the calibration and aperture calculation. The step of developing a geomechanical model and fracture drivers further includes determining a rock brittleness property of the core plug, performing a paleo-stress analysis on the core plug, developing a stress regime model, and performing a critical stress analysis on the core plug.

BRIEF DESCRIPTION OF THE DRAWINGS

So that the manner in which the features, advantages and objects of the invention, as well as others which may become apparent, are attained and can be understood in more detail, more particular description of the invention briefly summarized above may be had by reference to the embodiment thereof which is illustrated in the appended drawings, which drawings form a part of this specification. It is to be noted, however, that the drawings illustrate only example embodiments of the invention and is therefore not to be considered limiting of its scope as the invention may admit to other equally effective embodiments.

DETAILED DESCRIPTION

The methods and systems of the present disclosure can now be described more fully hereinafter with reference to the accompanying drawings in which embodiments are shown. The methods and systems of the present disclosure may be in many different forms and should not be construed as limited to the illustrated embodiments set forth herein; rather, these embodiments are provided so that this disclosure can be thorough and complete, and can fully convey its scope to those skilled in the art. Like numbers refer to like elements throughout.

Figure 1:
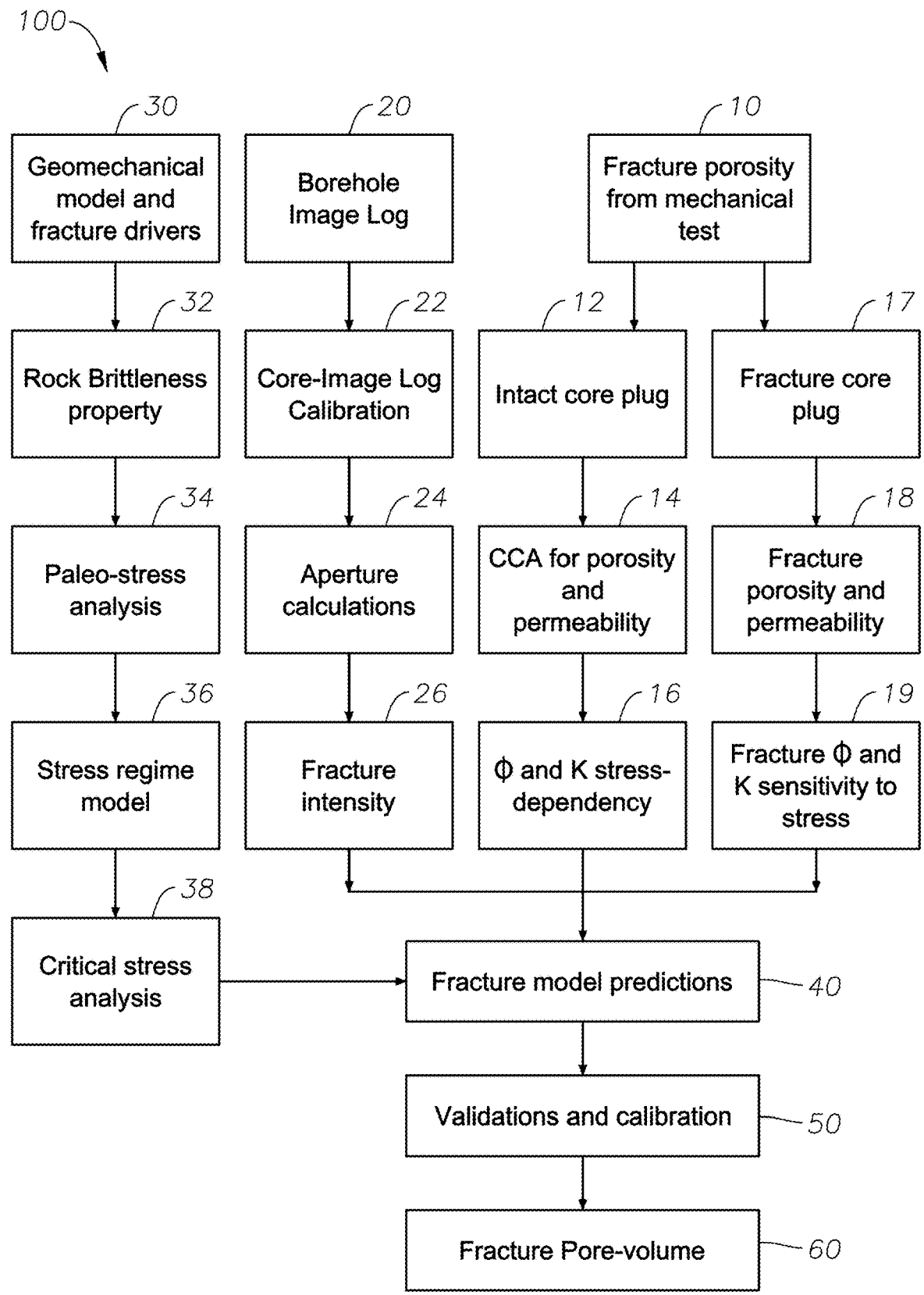
FIG. 1 is a flow chart illustrating example operations in a method for determining fracture porosity or fracture pore volume of a subsurface formation, according to one example embodiment of the disclosure.
Figure 2:
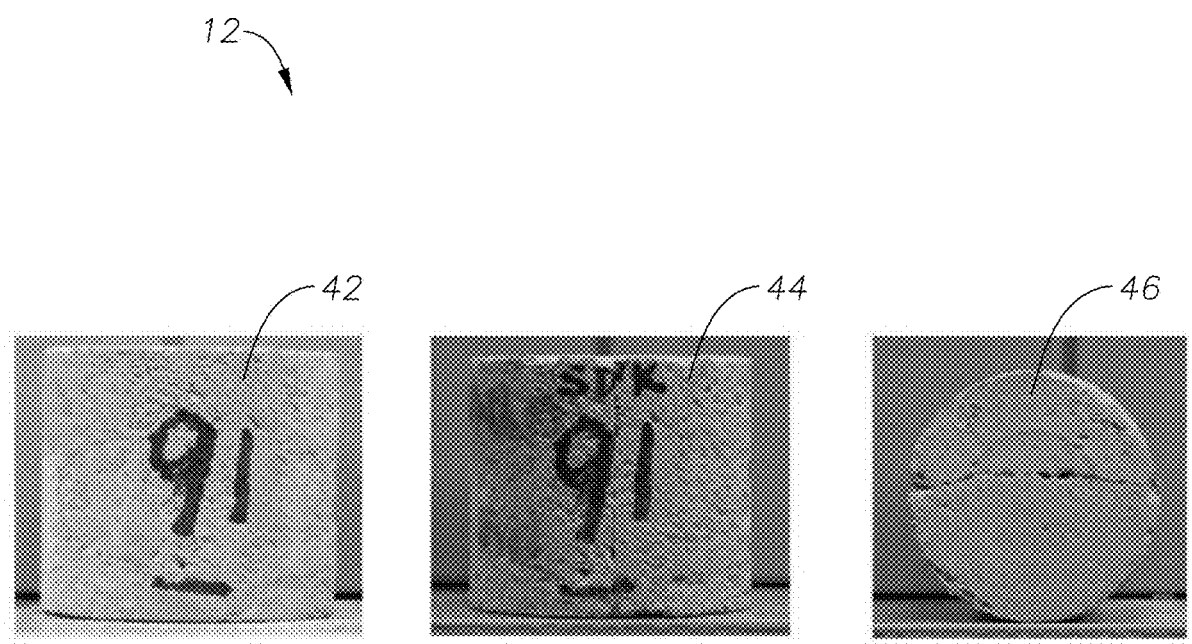
FIG. 2 shows photographs of an intact core plug (left) and core plugs with axial shear fracture (middle and right), according to one example embodiment of the disclosure.

Turning now to the figures, FIG. 1 is a flow chart illustrating example operations in a method 100 for determining fracture porosity or fracture pore volume of a subsurface formation, according to one example embodiment of the disclosure. The method is used to quantify the fracture porosity and fracture pore volume are based on mechanical laboratory measurements, aperture calculations, and intensity fracture calculated from borehole image logs, and these inputs are used to constrain the discrete fracture network. The method 100 has six main components as summarized in FIG. 1. More specifically, method 100 includes step 10 where fracture porosity of a core plug sample (of a subsurface formation) is determined from mechanical tests. This is a special mechanical test laboratory procedure designed to quantify the fracture porosity and permeability from a single core-plug specimen with a length-to-diameter ratio (L/D) between 2 to 2.5. The method is divided in two procedures: (1) related to the sample preparation and measurements performed on the intact core-plug, and (2) related to sample preparation and measurement performed after a shear fracture is propagated axially through the core-plug, as shown in FIG. 2. Under this innovative procedure, having the initial porosity at confined pressure conditions and the total porosity calculated from the core-plug with the fracture at confined pressure conditions, the fracture porosity can be subtracted.

FIG. 2 shows photographs of an intact core plug 42 and core plugs with axial shear fracture 44, 46, according to one example embodiment of the disclosure. The first step in core plug preparation or step 12 is selecting a number of plugs representative of the matrix formation in terms of bulk density, porosity, and permeability as well as a visual inspection to evaluate the shape and conditions of these plugs.

Plug preparation should be performed following standard procedures preferably ASTM Standard D4543-08. The preparation indicates a length-to-diameter ratio (L/D) for the core specimens of 2.0 to 2.5. Procedures for the determination of the elastic moduli on cylindrical specimens of rock are discussed in ASTM Standard D-7012-14.

Figure 3:
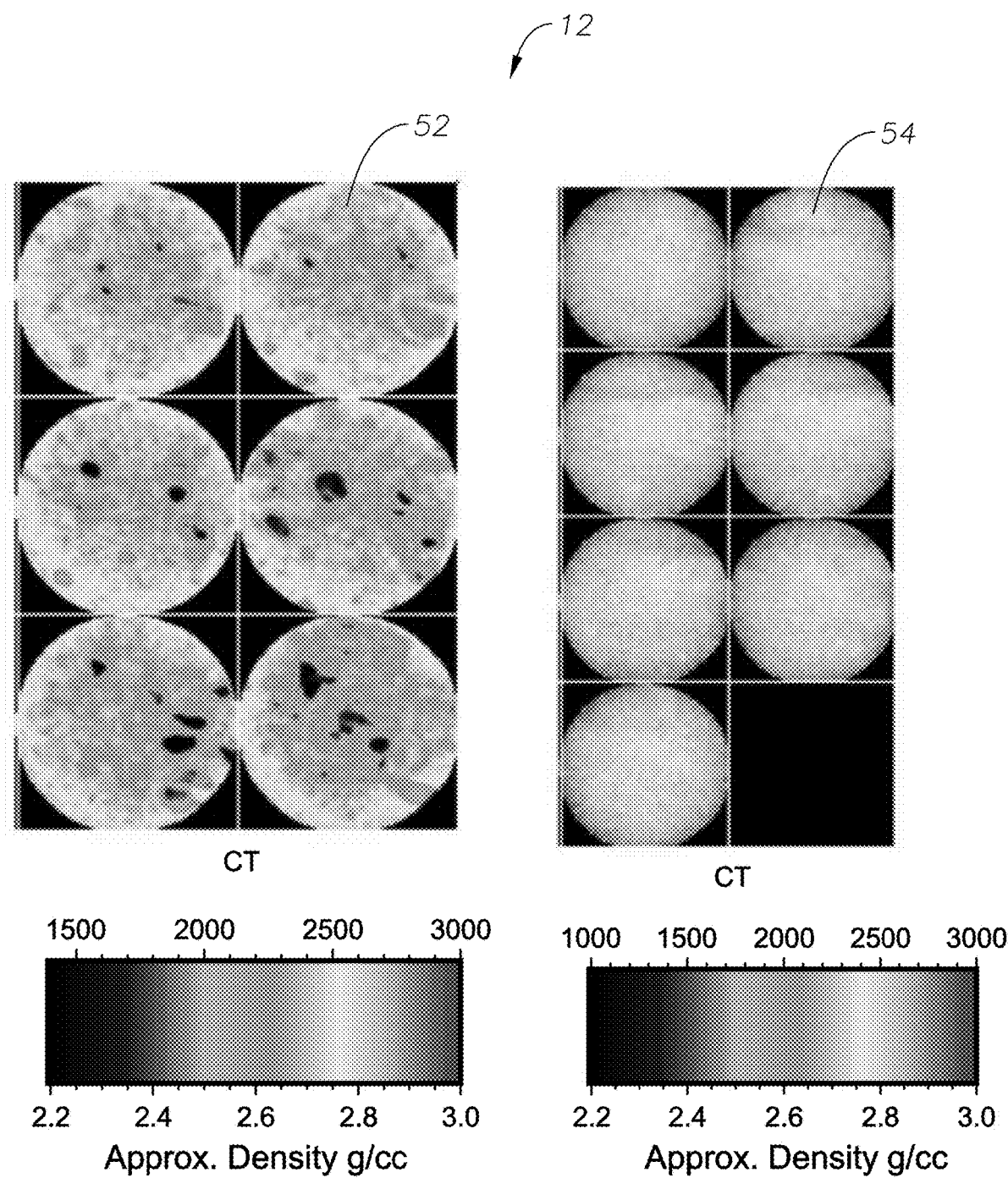
FIG. 3 illustrates computed tomography (CT) scans of a core plug showing scale density with one core plug including possible inclusions or vugs (left image) and a homogeneous core plug (right image), according to one example embodiment of the disclosure.

In this step 12, the core-plugs selected are scanned using a computerized tomographic (CT) scan machine to analyze internal structure of the plug matrix to detect possible discontinuities or inclusions inside the plugs that may affect the results. The CT scan evaluation may be performed based on density scale image as shown in FIG. 3, for example. These images could show dark areas that could represent vugs or irregular discontinuities in those case the sample might be discarded for the test. FIG. 3 illustrates computed tomography (CT) scans of a core plug showing scale density with one core plug including possible inclusions or vugs 52 and a homogeneous core plug 54, according to one example embodiment of the disclosure.

In step 14, a conventional core analysis (CCA) for porosity and permeability of the core plug is performed. This step may be performed to calculate the petrophysical properties for the intact core-plug, basic properties such as sample dimensions (L, D), sample weight, porosity, permeability and grain density should be measured. This step should follow the standard procedure widely used in the industry.

In step 16, determination of the porosity and permeability sensitivity to stress for the intact plug (matrix) is performed by means of testing in a servo-controlled rock mechanics tri-axial apparatus. The stress range for the tests included in this phase are defined based on estimates of the state of stress existing in the reservoir over its entire production life, from the initial (virgin) state to abandonment.

Additionally, pore volume compressibility (PVC) should be performed in order to evaluate the pore volume changes for several stress scenarios at hydrostatic conditions. Volume of water expelled by the specimen under increasing confining pressure is measured. Further, it is assumed that the volume of expelled water at time $t_1$ is equal to the total variation in pore space from to (start of the experiment) to $t_1$. This procedure is performed to determine a hydrostatic pore volume compressibility at changing confining pressure (Cpc) as defined in Zimmerman (R. W. Zimmerman, et al, "Compressibility of Porous Rocks", Journal of Geophysical Research, Vol. 91, No. B12, pp. 12,765-12,777, 1986).

The sample should be discarded in case the sample experiment plastic deformation during the test and if the sample show some anomalous values than expected during to the test such as anomalous porosity or permeability due to possible contamination.

Figure 4:
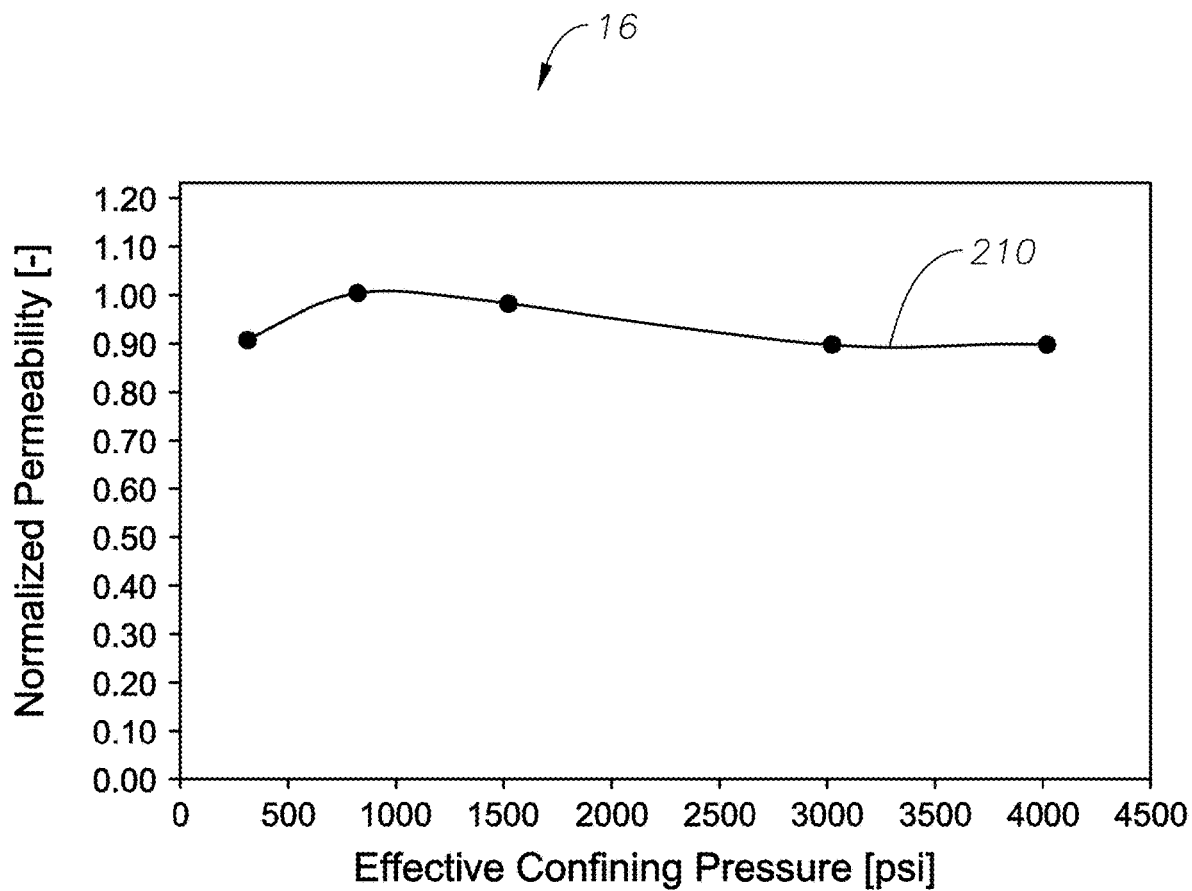
FIG. 4 illustrates stress dependent permeability of a matrix in a subsurface formation, according to some example embodiments of the disclosure.

In step 16, porosity and permeability dependency of the core plug are determined. Stress-dependent permeability testing determines the sensitivity to stress of the matrix permeability of the intact plug. A series of permeability measurements are performed at various states of stress defined as stations. The measurement stations are selected in order to cover the same stress interval over which the PVC test during the previous test defined. FIG. 4 illustrates stress dependent permeability of a matrix in a subsurface formation, according to some example embodiments of the disclosure.

In step 17, if there is a fracture core plug sample, a split plug is a plug with an approximately homogenous and continuous matrix with mode II (propagated by a shear stress acting parallel to the plane of the crack and perpendicular to the crack front) fracture propagated axially connecting the two ends of the specimen as shown in FIG. 2. This fracture could be created by tensile axial load following the standard ASTM D3967-08 or could be a natural fracture present already in the sample.

The core-plug sample is tested by mode II (shear fracture), these fractures are self-propped fractures meaning that the relative movement of the two halves of the fracture ensures that the topographies of opposite planes in the plug sample do not match. This in turn increases the hydraulic conductivity of the fracture even at increasing confining pressure. On the other hand, Mode I fractures are not self-propped, their conductivity is limited and may not contribute to the overall permeability of the rock.

In step 18, the basic petrophysical properties for the split plug (fracture) such as sample dimensions (L, D), sample weight and the total porosity are determined. Based on the total plug porosity (matrix+fracture) and on the matrix porosity measured at previous steps, fracture porosity can be derived through the equation:

$$\Phi_{Fracture} = \Phi_{Total} - \Phi_{Matrix}$$

This equation can be applied for each confined pressure applied within the PVC testing.

Figure 5:
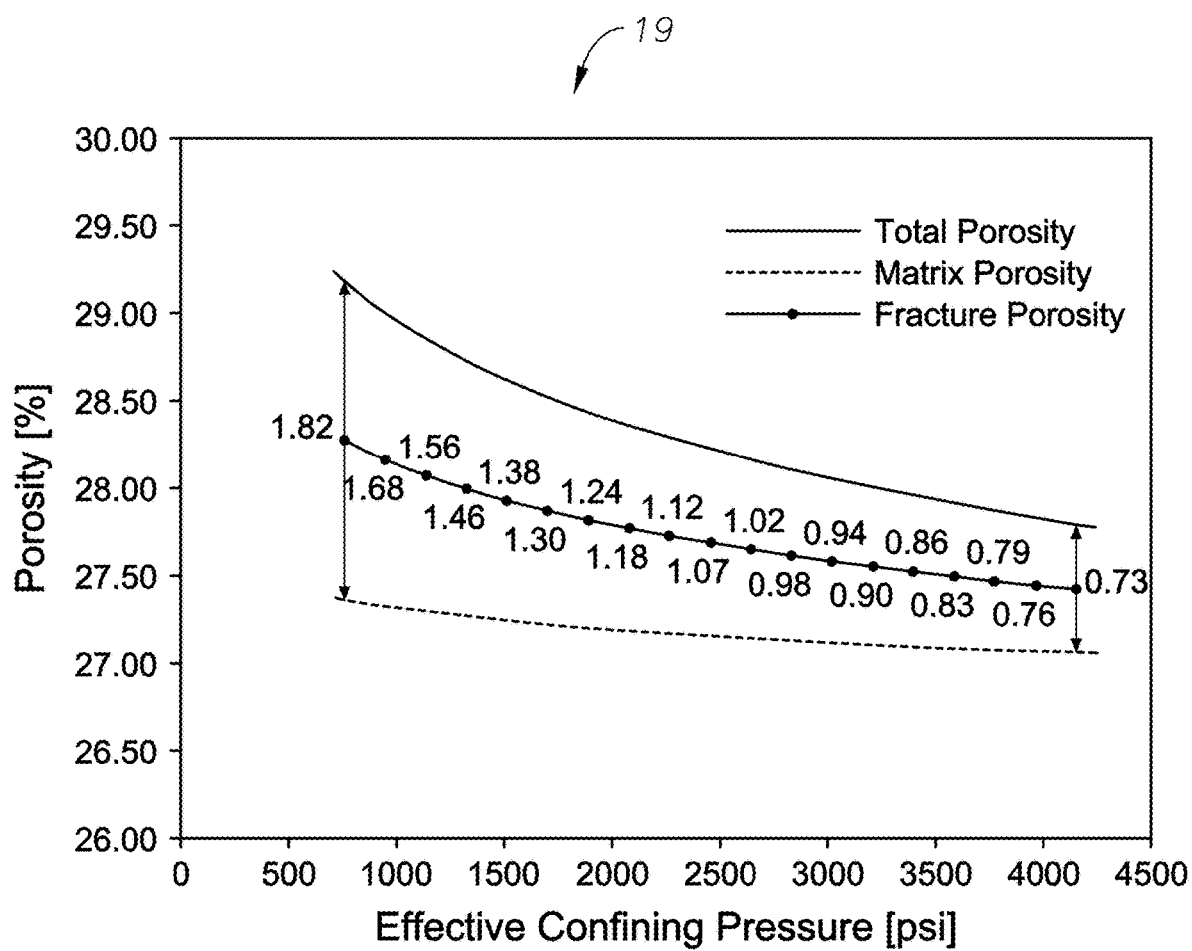
FIG. 5 illustrates a graph showing fracture porosity subtracted from intact and split core plugs at confined pressure conditions, according to some example embodiments of the disclosure.

In step 19, determination of the fracture porosity sensitivity to stress during is performed by testing in a servo-controlled rock mechanics tri-axial apparatus. The stress range for the tests included for the matrix (intact plug) tests to be able to compare. The determination of the fracture porosity related to stress changes can be performed by halting between the PVC at pre-determined stress stations (cycles) and permeability measurements at same stress stations imposed by confining pressure. The PVC stations is then re-started until a new station is reached. The measurements must be performed within the elastic domain avowing to reach the plastic behavior. FIG. 5 illustrates a graph showing fracture porosity subtracted from intact and split core plugs at confined pressure conditions or the relative changes between the porosity from the intact core-plug and split core-plug sample controlled by the confined pressure stages, according to some example embodiments of the disclosure.

Step 20 involves receiving borehole image logs. Borehole resistive image log (BHI) can provide full natural fracture description including natural fracture type, dip angle, dip azimuth and intensity along of the wellbore. The BHI log can be also used to estimate the apparent aperture using a normalized resistive image and shallow resistivity log (Rxo).

Figure 6:
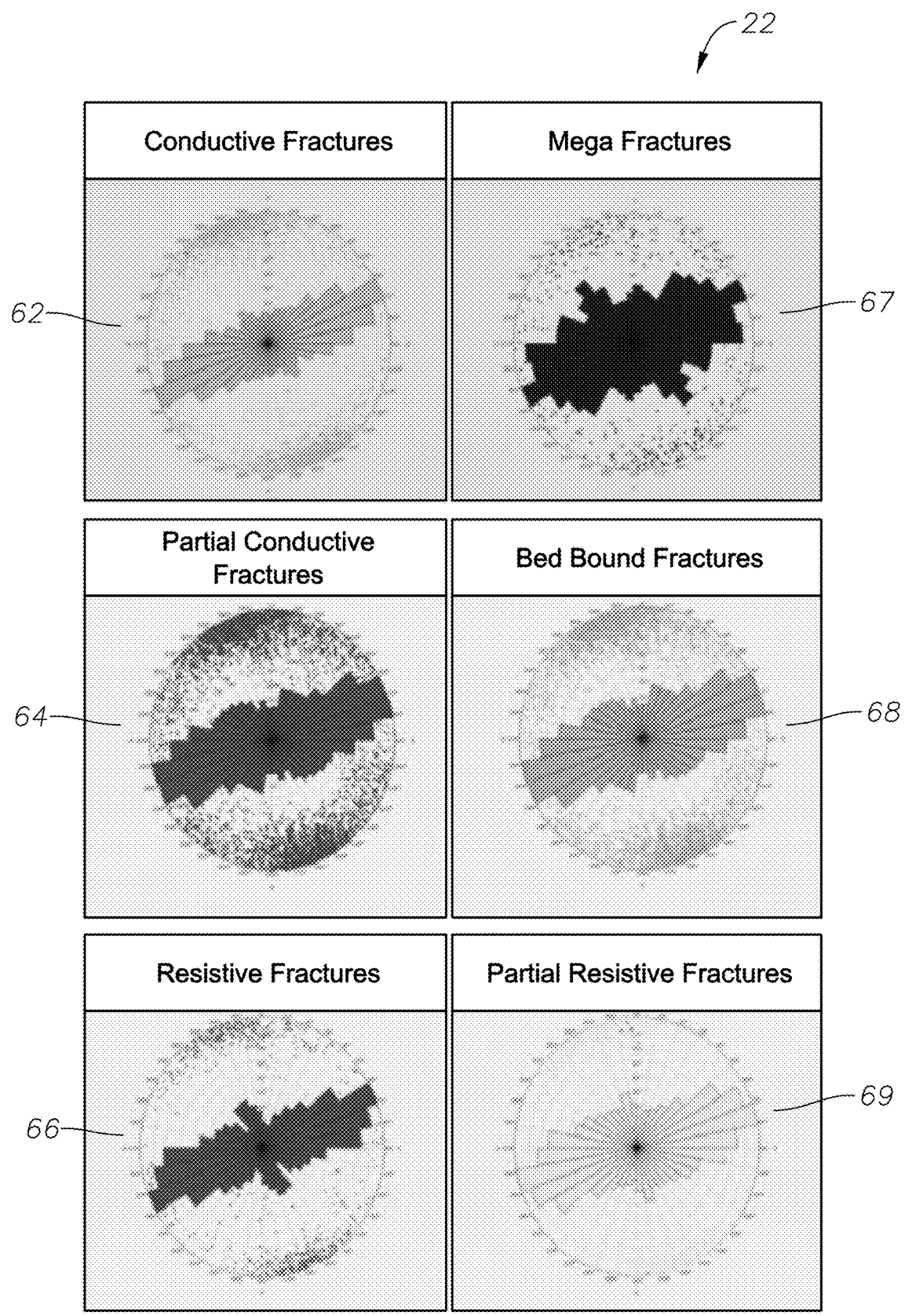
FIG. 6 illustrates classification of fracture types, according to some example embodiments of the disclosure.

FIG. 6 illustrates classification of fracture types 22, which is a step under core image calibration. For example, the fracture types 22 may include conductive fractures 62, mega fractures 67, partial conductive fractures 64, bed bound fractures 68, resistive fractures 66, and partial resistive fractures 69. The fracture identified using borehole image resistive log can be calibrated qualitatively with the natural fractures described from whole core. These cores are extracted from a wellbore and depends of the quality and coverage to be compare with the BHI. The comparison between the BHI and whole core could be related to the fracture intensity, fracture mineralization, fracture orientations and types mainly. Within the type's fractures may interpreted as mega fractures, conductive fractures, partially conductive, resistive fracture and partial resistive fractures as shown in FIG. 6.

Figure 7:
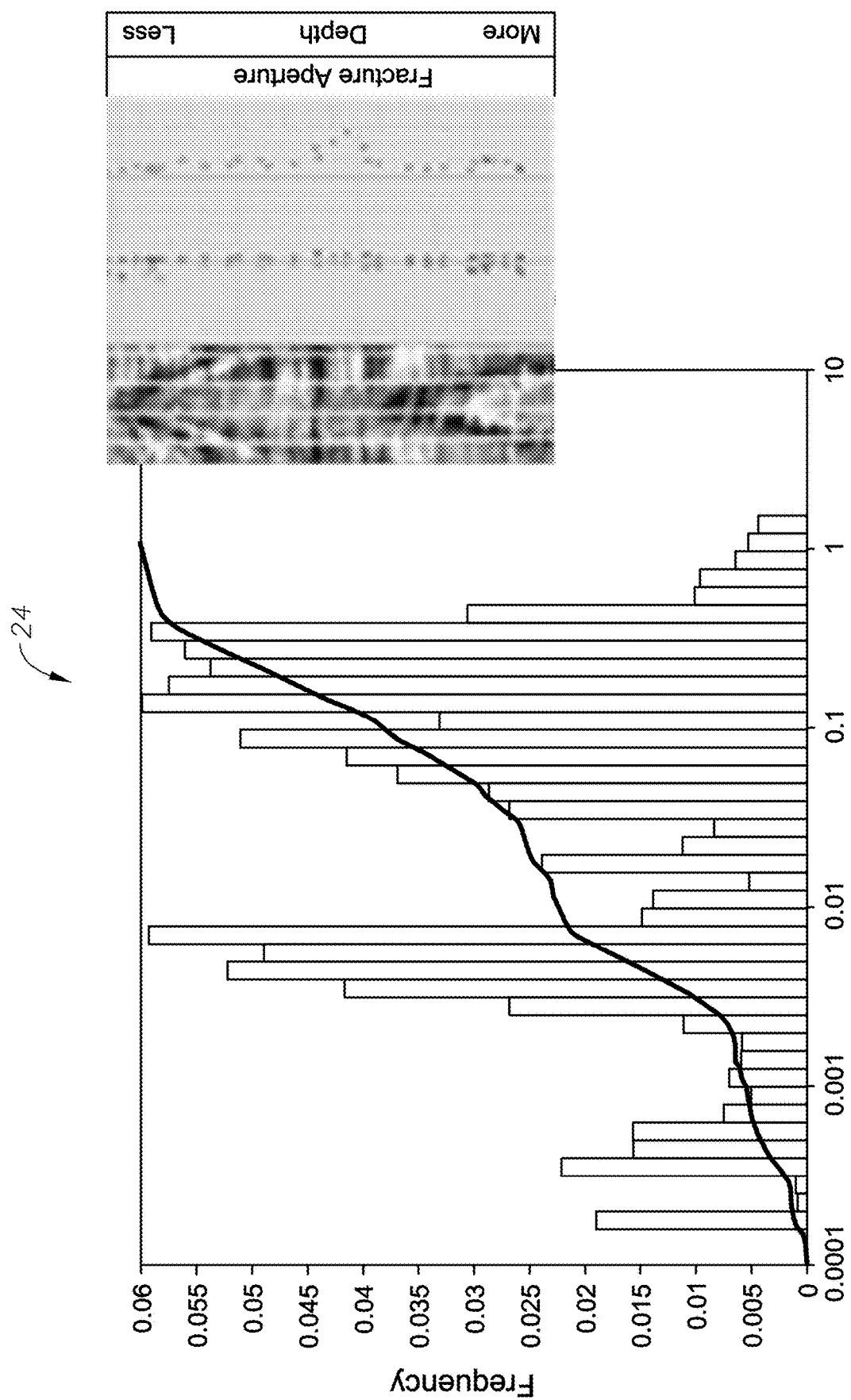
FIG. 7 illustrates a graph showing fracture aperture distribution with a subsurface formation, according to one example embodiment of the disclosure.

Step 24 involves aperture calculations are based on borehole resistive image log as shown in FIG. 7. The aperture of fractures interpreted by using electrical imaging tools in water-based mud can be calculated based on the equation proposed by Luthi S. M. and Souhaite, P.

$$W = cAR_m^b R_{xo}^{1-b}$$

The equation describes the relationship between fracture width W, flushed zone resistivity $R_{xo}$, mud resistivity $R_m$ and the excess current A, flowing into the matrix through the conductive media due to the presence of the fracture. The excess current is a function of fracture width. The quantity of which is estimated by statistical and geometrical analysis of the anomaly that it creates compared to the background conductivity. The coefficient c, and the exponent b are tool-specific and numerically obtained values. The method can be directly applied to on formation micro-resistivity image (FMI) and FMS data. Usually the aperture is represented by millimeters as unit. FIG. 7 illustrates a graph showing fracture aperture distribution with a subsurface formation, according to one example embodiment of the disclosure.

Figure 8:
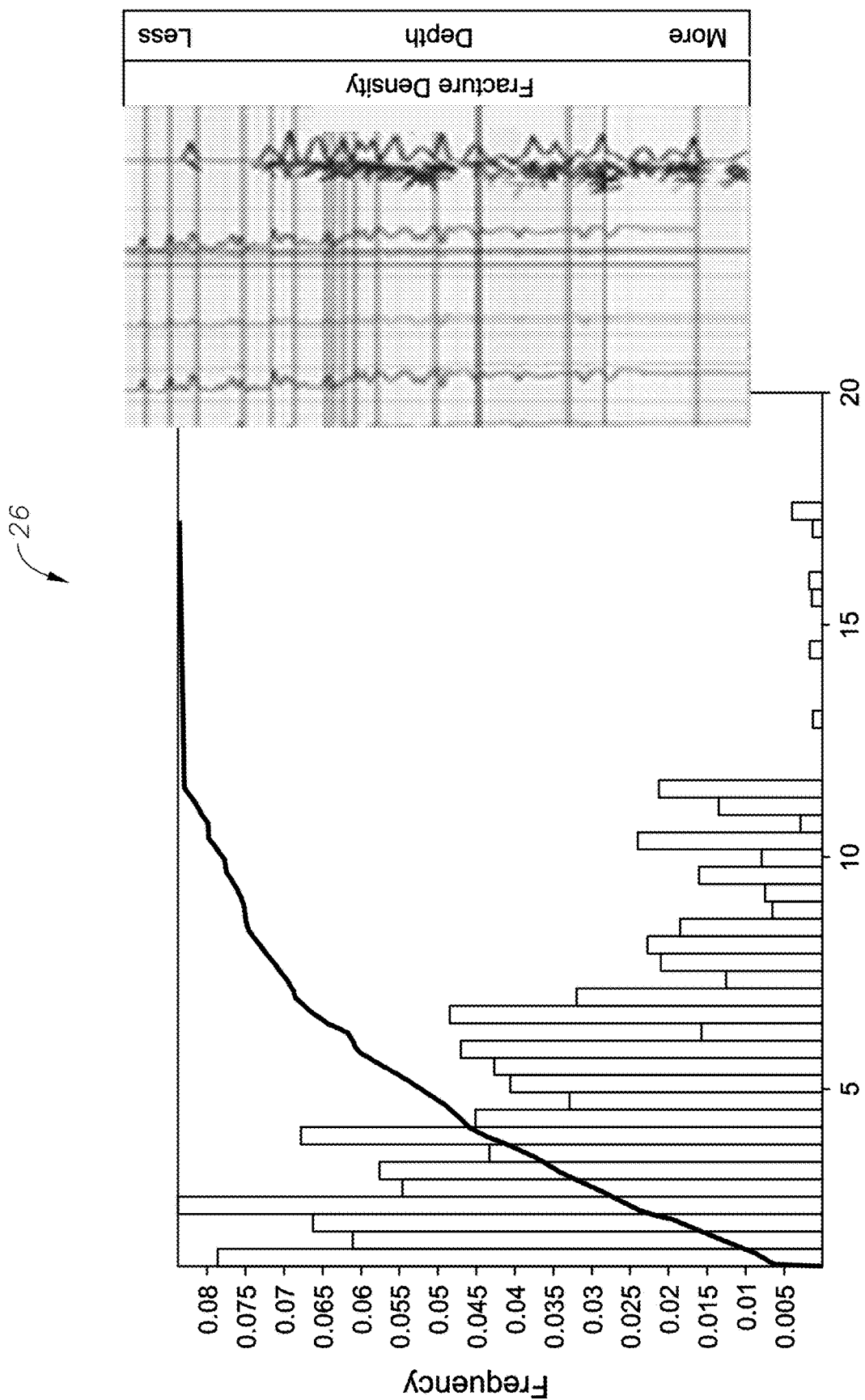
FIG. 8 illustrates a graph showing fracture intensity distribution with a subsurface formation, according to one example embodiment of the disclosure.

In step 26, once the fracture interpretation is completed a set of natural fractures is obtained according with the classification, then the fracture intensity can be quantified by establishing a windows and log sample to count the fracture by depth, as shown in FIG. 8, which illustrates a graph showing fracture intensity distribution with a subsurface formation, according to one example embodiment of the disclosure.

Step 30 involves determining a geomechanical model and fracture drivers for the core plug. At 3D grid stage, geomechanics numerical simulation are performing using finite and boundary elements geomechanics simulation methods to be able to capture the main episodes for paleo-stress tectonic deformation that could create most of the fracture observed at well level; those fracture is modeled following mainly two process: folding fracture related, and faulting fracture related. Additionally, the in-situ stress regime must be modeled capturing the features related to mechanical properties such as brittleness model, geomechanical facies, in-situ stress rotations and stress magnitude variation along of the field.

Figure 9A:
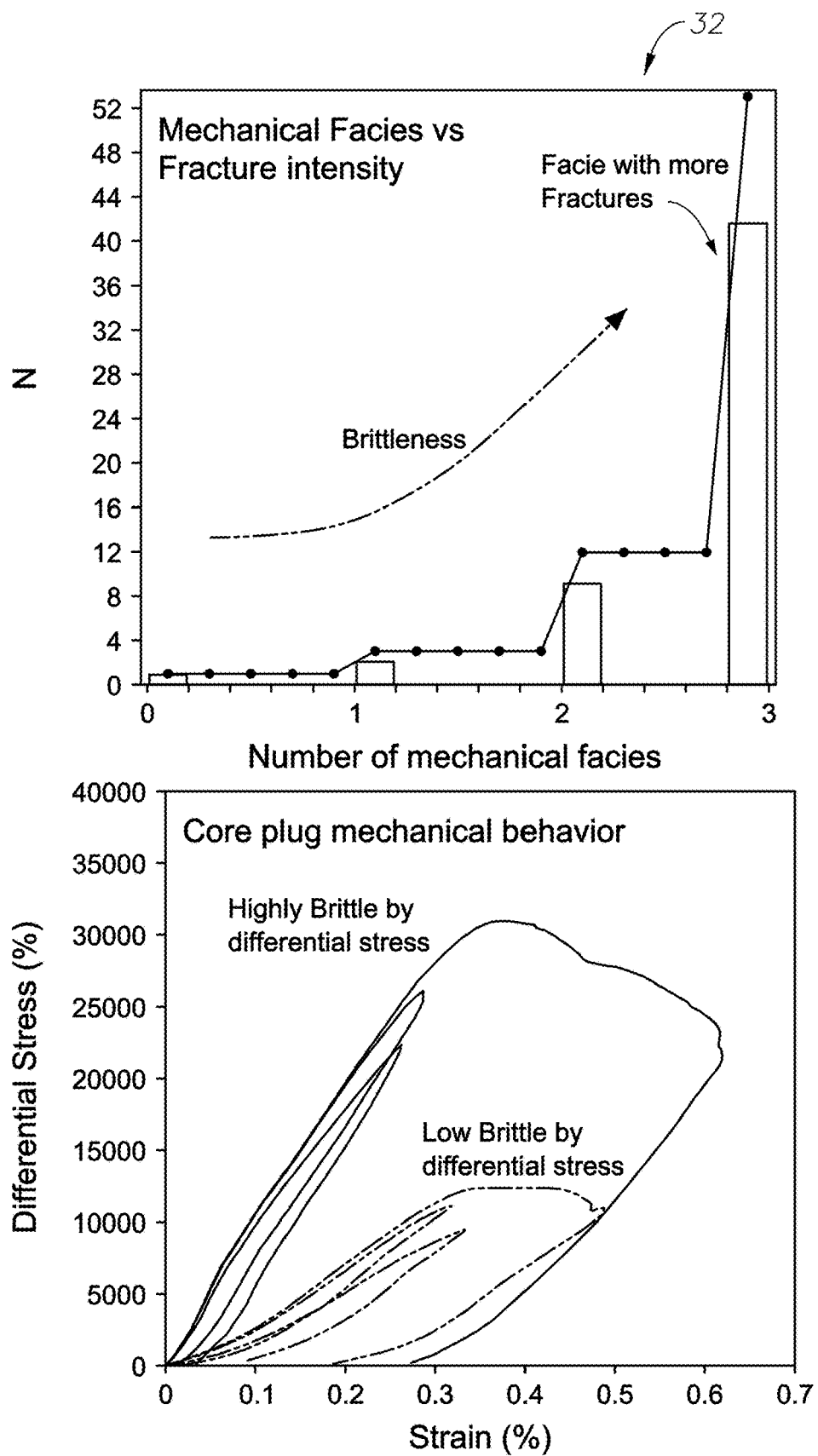
FIGS. 9A and 9B illustrate a graph showing natural fracture distribution by mechanical facies in a subsurface formation, according to one example embodiment of the disclosure.
Figure 9B:
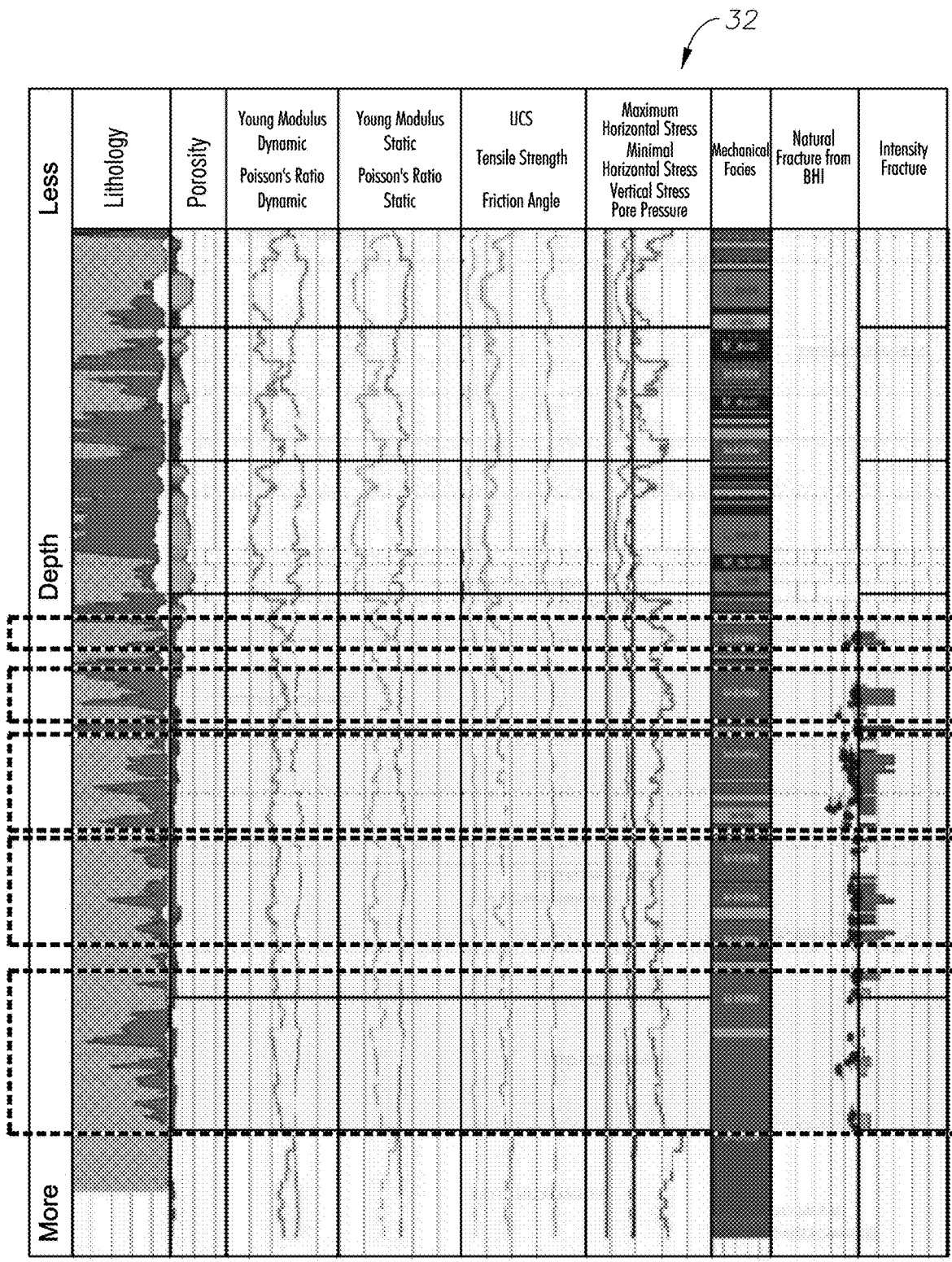

At step 32, a rock brittleness property can be differentiated when is subjected to stress, it breaks without significant plastic deformation. Brittle materials absorb relatively little energy prior to fracture, even those of high strength. In a complex heterogeneous fracture rock mass, the brittleness property can be modeled using neuronal network classification taking as inputs the elastic properties and stress regime producing mechanical facies. Those mechanical facies, certainly, should have some proportional relation with the distribution of natural fractures, this correlation can be evaluated using histogram filtered by density fracture, as shown in FIGS. 9A and 9B, which illustrate graphs showing natural fracture distribution by mechanical facies in a subsurface formation, according to one example embodiment of the disclosure.

At step 34, a paleo-stress analysis is conducted. The geomechanical restoration process can be used to calculated stress and strain paleo-stress deformation analyzing each geological tectonic episode. This analysis probably needs distinguish between the fractures created by folding process or by faulting process, creating possible strain/stress deformation for each process. This process, regarding the fractures folding relation maybe could be modeled using geomechanical restoration (i.e. Kine3D, Move, etc.) and the faulting response maybe modeled using boundary element method (BEM) which are incorporate into Petrel software iBEM3D (Maerten, 2009).

At step 36, a stress regime model is developed. The "In-situ" stress regime can be modeled using FEM software (Finite Element Model) techniques, which can predict the stress/strain tensor regime using mechanical boundary elements. FEM methods use geomechanics simulations to converge a proper solution under certain boundary stress conditions. Maximum principal horizontal stress model and magnitude can be obtained from this methodology for each cell into the 3D Grid geo cellular model (Herwanger et al., 2011). There are several software applications to model stress regime such as Visage, Abaqus, etc.

Figure 10B:
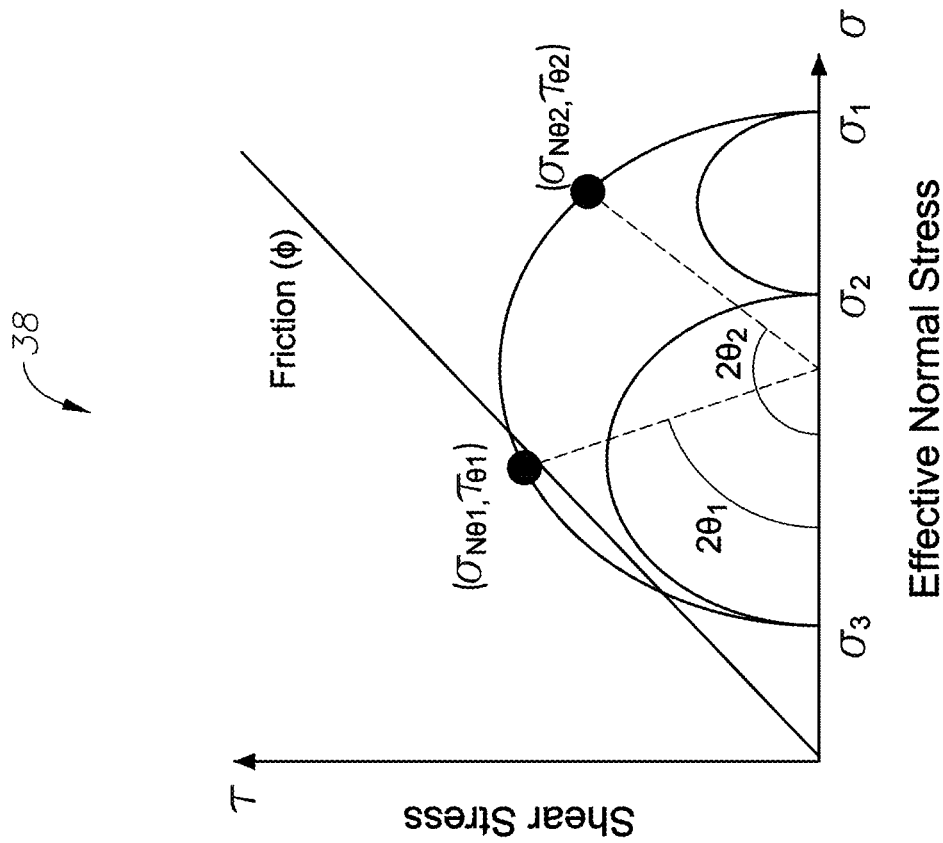
FIGS. 10A and 10B illustrate a graph showing critical stress for natural fractures in a subsurface formation, according to one example embodiment of the disclosure.
Figure 10A:
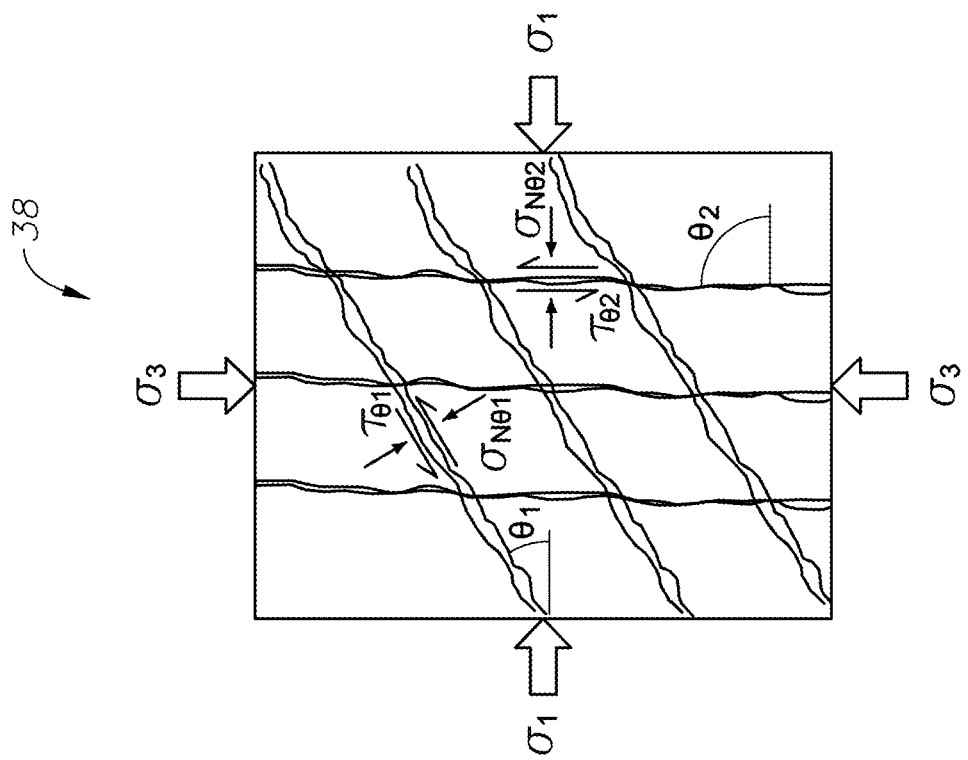

FIGS. 10A and 10B illustrates a graph showing critical stress for natural fractures in a subsurface formation, according to one example embodiment of the disclosure. At step 38, a critical stress analysis is performed. Critical stress concept criteria are used in this methodology following the Coulomb criterion, which depends on the stress magnitude and the orientation of the fracture plane with respect to the "In situ" stress orientation. The orientation affects the normal and shear stresses on the fracture plane. When shear stress exceeds shear stiffness, shearing cause's dilation that keeps the fracture hydraulically open [Rogers, 2003]. Fractures in this stress state are referred to be reactivated or critically stressed [Barton et al., 1995; Rogers, 2003] showing in FIGS. 10A and 10B.

$$\text{Critical fractures} = (\tau - \sigma_n * \text{Tan}(\varphi)) \geq 0$$

Figure 11:
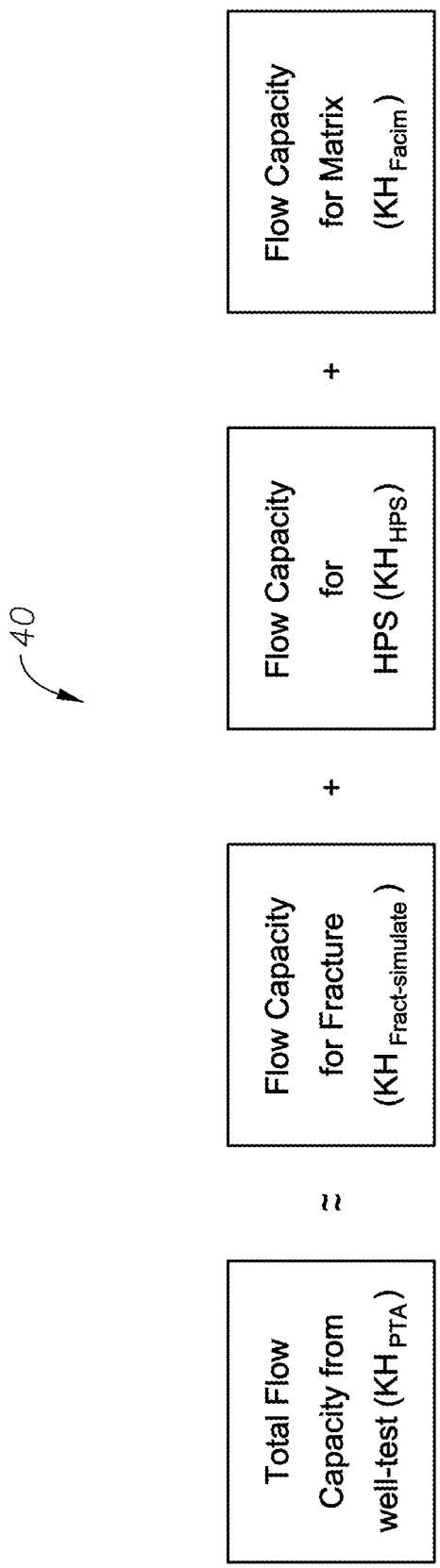
FIG. 11 illustrates a formula for determining flow capacity of each element contributing to the fluid flow in a subsurface formation, according to one example embodiment of the disclosure.

Step 40 involves making fracture model predictions. FIG. 11, for example, illustrates a formula for determining flow capacity of each element contributing to the fluid flow in a subsurface formation, according to one example embodiment of the disclosure. Discrete fracture network realizations are constrained by geomechanical drivers. The parametrization of the main variables to constrain the fracture presence or position within the 3D geo-cellular grid model such as fracture density, length, orientation and geometry (Length/Height) are controlling by borehole image log interpretation (BHI), brittleness property, paleo-stress tectonic analysis and "In-situ" stress regime. However, the fracture aperture for the fracture model can be constrained by using the aperture calculations from borehole image. The intrinsic permeability can be modeled (permeability values assigned to the fracture plane using initial correlations such as cubic law function) by using the critical stress analysis, which related the stress distribution and the fracture planes in terms of hydraulic permeability, the method is described by Ki-Bok Min et al. using stress-dependent permeability model for fractures. The equivalent medium to represent the natural fracture network into a 3D grid block can be performed by doing scale-up process (available in Petrel™ and other softwares) which allows us to calculate by grid block the effective permeability tensor, sigma factor (transfer function between the matrix and fractures) and fracture porosity. At this stage the fracture porosity from the equivalent medium can be calibrated using the results obtained from fracture porosity estimations from split core-plug.

Step 50 involves validation and calibration of the models, for example. Reservoir dynamic data are integrated at this stage to validate the fracture models realizations, dynamic data such as pressure transient analysis (PTA), Production log test (PLT), tracers, water encroachment, cumulative production, etc. has been used to calibrate the model in the qualitative (i.e. blind test) and quantitate (i.e. KH quantification) way. Multiple realizations can be performed in order to optimize the results by reducing the difference between the flow capacity from the pressure transient analysis ($KH_{PTA}$) and the total flow capacity produce by each component of the geological model (Fractures $KH_{Fract-simulate}$, Matrix $KH_{Facim}$ and High Permeability Streak $KH_{HPS}$) as shown in FIG. 11.

A hierarchy was established to calculate the equivalent permeability for the three components, where the fractures have the major impact for the fluid flow movement followed by HPS (High Permeability Streak) and matrix. Using this hierarchy, the flow capacity can be calculated for each component and optimized using the Genetic Algorithms (GA) develop into a petrel plugin in order to reduce within each iteration the difference between the flow capacities predicted and measured, as shown in FIG. 11.

Figure 12:
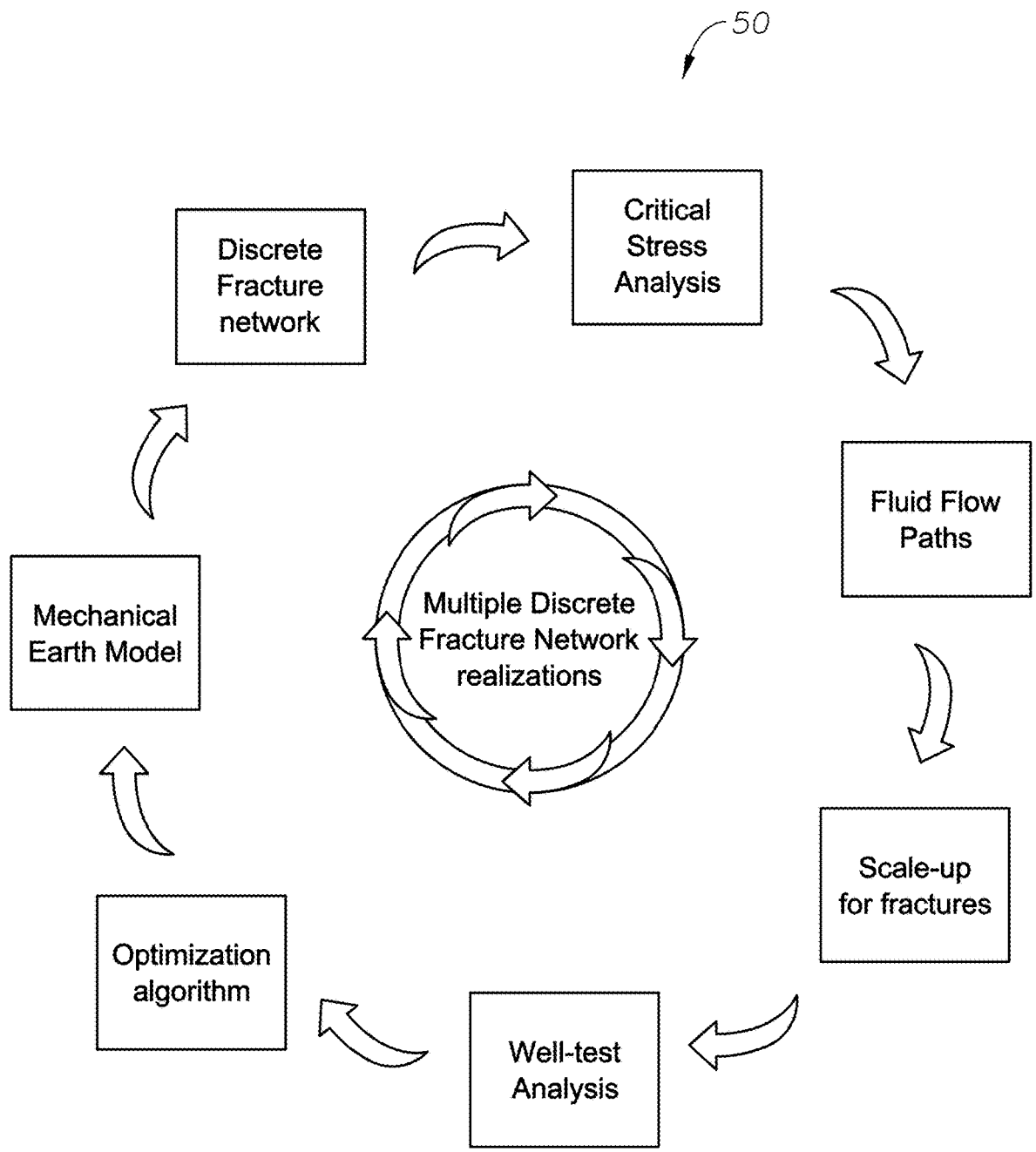
FIG. 12 illustrates a flow diagram for example steps involved in determining fracture and reservoir properties in multiple fracture realizations, according to one example embodiment of the disclosure.

FIG. 12 illustrates a flow diagram for example steps involved in determining fracture and reservoir properties in multiple fracture realizations, according to one example embodiment of the disclosure. A workflow for multiple fracture realization can be use as part of validations and calibration. The impact of critically stressed aperture and permeability on fluid flow is quantified using equivalent permeability, which considers fracture, HPS, and matrix flow and the interaction between the three. For example, step 50 may include multiple discrete fracture network realizations including a well-test analysis, an optimization algorithm, a mechanical earth model, discrete fracture network, critical stress analysis, determining fluid flow paths, and scaling up for fractures, as illustrated.

Figure 13:
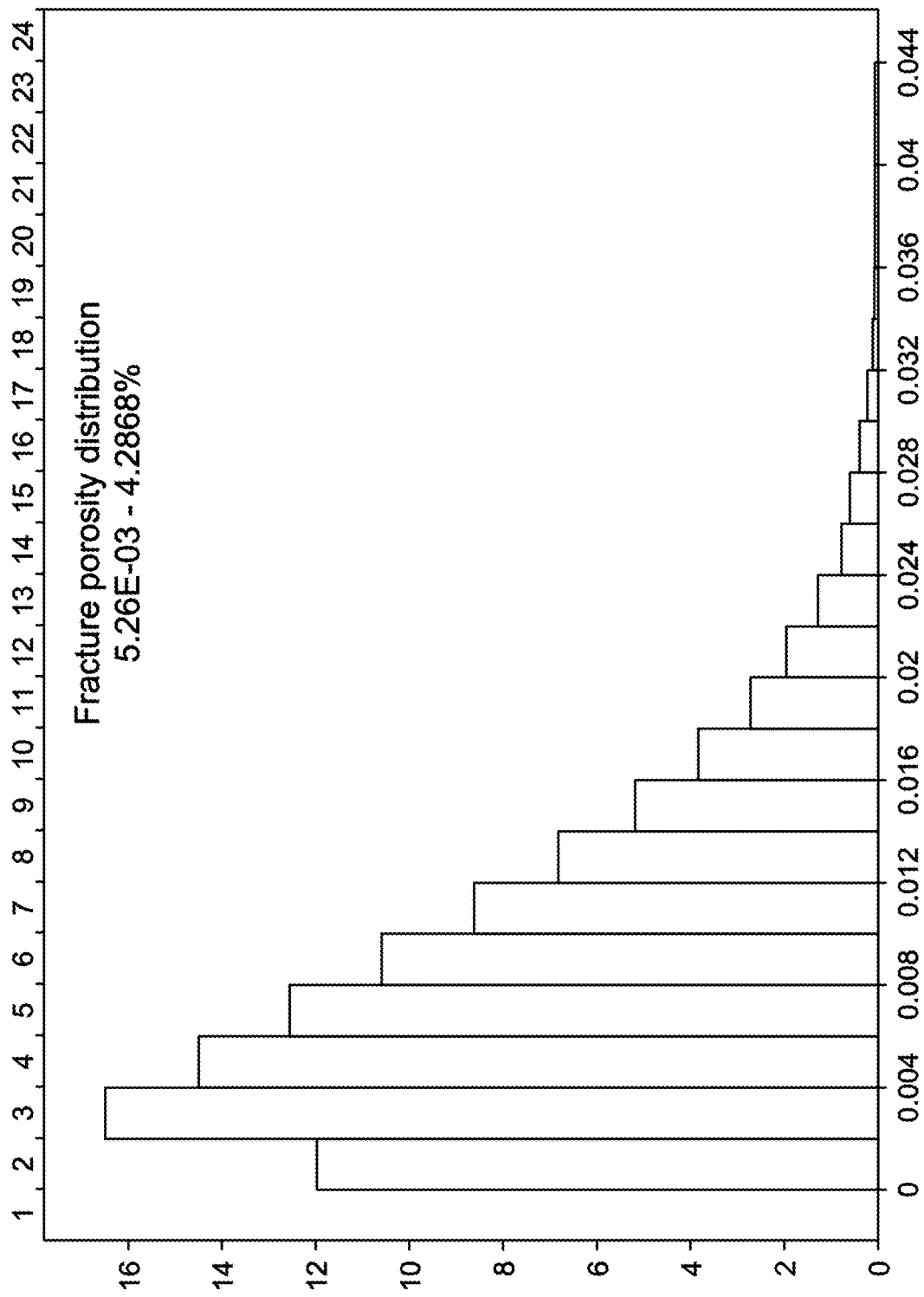
FIG. 13 illustrates a graph showing fracture porosity distribution in a core plug sample, according to one example embodiment of the disclosure.

Lastly, in step 60, the fracture pore-volume is calculated taking the rock bulk volume multiplied with the fracture porosity model that is constrained by the values calculated with the core-plug fracture porosity estimations. Additionally, reserves for natural fractures can be estimated assuming that the natural fractures are discontinuity elements that might not present capillarity and assumption such as water saturation equals to zero for grid blocks contained natural fractures is a good approach to calculate the fluid "In-Place". FIG. 13 illustrates a graph showing fracture porosity distribution in a core plug sample, according to one example embodiment of the disclosure.

Computer Readable Medium

Figure 14:
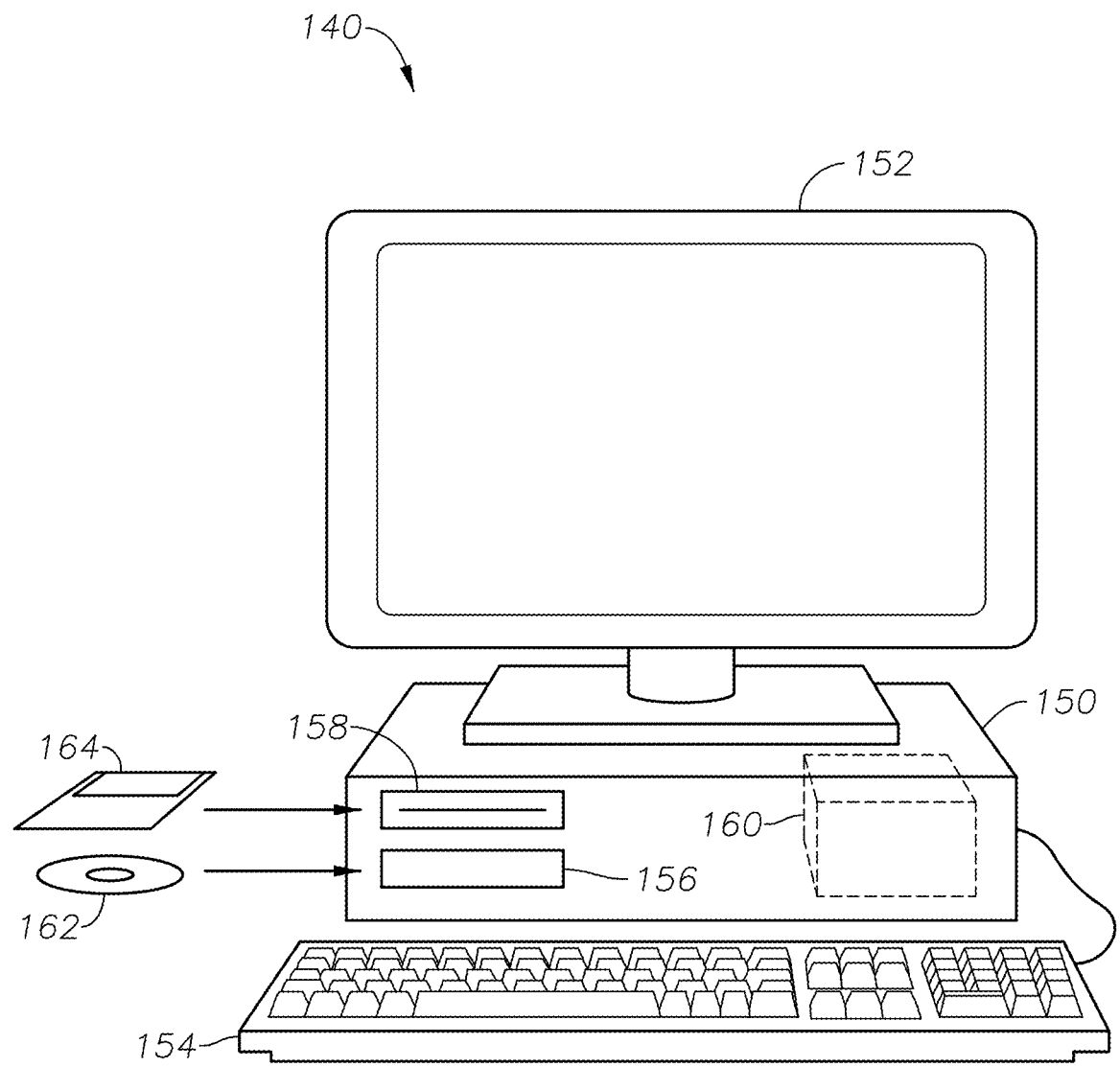
FIG. 14 shows a programmable computer and various forms of computer readable media, according to some example embodiments of the disclosure.

In another example embodiment, the invention relates to computer programs stored in computer readable media. Referring to FIG. 14, the foregoing process as explained with reference to FIGS. 1-13 can be embodied in a computer-readable code, e.g. any of the example software mentioned above, either alone or in combination. The code can be stored on, e.g., a computer readable medium, such as a floppy disk 164, CD-ROM 162 or a magnetic (or other type) hard drive 160 forming part of a general purpose programmable computer 140. The general purpose computer 140 may include disc drives 158 and 156, which may be configured to read a computer readable medium, such as a floppy disk 164, CD-ROM 162, respectively, and execute the computer code thereon. The computer 140, as known in the art, includes a central processing unit 150, a user input device such as a keyboard 154, and a user display 152 such as a flat panel LCD display or cathode ray tube display. According to this aspect of the invention, the computer readable medium includes logic operable to cause the computer to execute acts as set forth above and explained with respect to the FIGS. 1-13. The non-transitory computer-readable medium having computer executable instructions cause a computer or processor to perform the operations of. Although a standalone general purpose programmable computer 140 is illustrated in FIG. 14, it may be apparent to one of ordinary skill in the art that computer 140 may be connected one or more other computers via a wired or wireless network, and may form part of a larger networked environment.

Accordingly, the present disclosure discloses methods for obtaining fracture porosity and introducing the fracture porosity in the model. The disclosure more specifically relates to a comprehensive method to calculate fracture porosity from rock mechanical test combined with resistive image log. The fracture porosity relies on calculation based on formation micro-resistivity image (FMI) log method by calculating the fracture apertures geo mechanical-constrained and translated into a 3D grid model used as equivalent fracture media in order to assign the calculated fracture porosity. The present disclosure relates to naturally fracture reservoirs as well as the estimation of pore-volume for natural fractures by utilizing a comprehensive methodology.

The Specification, which includes the Summary, Brief Description of the Drawings and the Detailed Description, and the appended Claims refer to particular features (including process or method steps) of the disclosure. Those of skill in the art understand that the invention includes all possible combinations and uses of particular features described in the Specification. Those of skill in the art understand that the disclosure is not limited to or by the description of embodiments given in the Specification.

Those of skill in the art also understand that the terminology used for describing particular embodiments does not limit the scope or breadth of the disclosure. In interpreting the Specification and appended Claims, all terms should be interpreted in the broadest possible manner consistent with the context of each term. All technical and scientific terms used in the Specification and appended Claims have the same meaning as commonly understood by one of ordinary skill in the art to which this invention belongs unless defined otherwise.

As used in the Specification and appended Claims, the singular forms "a," "an," and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced. The verb "operatively connecting" and its conjugated forms means to complete any type of required junction, including electrical, mechanical or fluid, to form a connection between two or more previously non-joined objects. If a first component is operatively connected to a second component, the connection can occur either directly or through a common connector. "Optionally" and its various forms means that the subsequently described event or circumstance may or may not occur. The description includes instances where the event or circumstance occurs and instances where it does not occur.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language generally is not intended to imply that features, elements, and/or operations are in any way required for one or more implementations or that one or more implementations necessarily include logic for deciding, with or without user input or prompting, whether these features, elements, and/or operations are included or are to be performed in any particular implementation.

The systems and methods described herein, therefore, are well adapted to carry out the objects and attain the ends and advantages mentioned, as well as others inherent therein. While example embodiments of the system and method have been given for purposes of disclosure, numerous changes exist in the details of procedures for accomplishing the desired results. These and other similar modifications may readily suggest themselves to those skilled in the art, and are intended to be encompassed within the spirit of the system and method disclosed herein and the scope of the appended claims.

The invention claimed is:

1. A method for determining properties of a subsurface formation comprising:
   obtaining an intact core plug sample and a fractured core plug sample from the subsurface formation;
   conducting a first mechanical laboratory test on the intact core plug sample that comprises performing a conventional core analysis for porosity and permeability of the intact core plug sample, and determining a matrix porosity and a matrix permeability sensitivity to stress for the intact core plug sample at confined pressure conditions;
   conducting a second mechanical laboratory test on the core plug sample after it has been fractured, that comprises performing the conventional core analysis for porosity and permeability of the fractured core plug sample, and determining a total porosity and a total permeability sensitivity to stress for the fractured core plug sample at the pressure conditions;
   determining a fracture porosity for the fractured core plug sample based on the matrix porosity and the total porosity;
   determining a fracture permeability sensitivity to stress for the fractured core plug sample based on the matrix permeability sensitivity to stress and the fracture permeability sensitivity to stress;
   obtaining a borehole image log interpreted by using an electrical imaging tool;
   determining a plurality of fracture features for the subsurface formation by performing aperture calculations of the subsurface formation using the borehole image log;
   determining a geomechanical model and one or more fracture drivers for the fractured core plug sample based on the plurality of fracture features and the fracture porosity;

performing, using the geomechanical model and the one or more fracture drivers, fracture model predictions for a plurality of discrete fracture network realizations to determine a fracture porosity model associated with the subsurface formation;

calculating a fracture pore volume in the subsurface formation based on the fracture porosity model and a rock bulk volume associated with the subsurface formation; and estimating oil gas reserves in the subsurface formation based on the fracture pore volume.

2. The method of claim 1, further comprising:

fracturing the core plug sample by tensile axial load following the standard ASTM D3967-08.

3. The method of claim 2, further comprising deriving fracture porosity by subtracting the matrix porosity from the total porosity.

4. The method of claim 3, wherein the step of analyzing borehole image logs further comprises:

determining fracture intensity based on a calibration of the borehole image log and aperture calculation.

5. The method of claim 3, wherein the step of developing the geomechanical model and one or more fracture drivers further comprises:

determining a rock brittleness property of the core plug sample;

performing a paleo-stress analysis on the core plug sample;

developing a stress regime model; and performing a critical stress analysis on the core plug sample.

6. The method of claim 1, wherein the core plug sample is extracted from a subsurface formation comprising at least one of shale, limestone, and sandstone.

7. The method of claim 1, wherein the plurality of fracture features comprise natural fracture type, dip angle, dip azimuth, and intensity along of a wellbore.

8. The method of claim 1, further comprising:

determining the geomechanical model by applying geomechanics numerical simulation using finite and boundary elements geomechanics simulation methods.

9. The method of claim 1, wherein the plurality of discrete fracture network realizations comprise a well-test analysis, an optimization algorithm, a mechanical earth model, discrete fracture network, critical stress analysis, determining fluid flow paths, and scaling up for fractures.

10. The method of claim 1, wherein the plurality of discrete fracture network realizations are performed based on the plurality of fracture features for the fractured core plug sample, the fracture porosity for the fractured core plug sample, and the fracture permeability sensitivity to stress for the fractured core plug sample.

11. The method of claim 1, wherein the plurality of discrete fracture network realizations are optimized to reduce a difference between a predicted flow capacity and a measured flow capacity.

12. The method of claim 11, wherein:

the measured flow capacity comprises a flow capacity from a pressure transient analysis (KHPTA), and the predicted flow capacity comprises a total flow capacity which is a sum of a flow capacity associated with fractures (Fractures KHFract-simulate), a flow capacity associated with High Permeability Streak (High Permeability Streak KHHPS), and a flow capacity associated with matrix (Matrix KHFacim).

* * * * *